United States Patent

Hammar et al.

[11] Patent Number: 5,273,559
[45] Date of Patent: Dec. 28, 1993

[54] ABRASIVE DENTAL ARTICLES

[75] Inventors: W. James Hammar, St. Paul; Richard W. Joos, Eagan, both of Minn.

[73] Assignee: Minnesota Mining and Manufacturing Company, St. Paul, Minn.

[21] Appl. No.: 992,014

[22] Filed: Dec. 17, 1992

Related U.S. Application Data

[63] Continuation of Ser. No. 753,204, Aug. 30, 1991, abandoned.

[51] Int. Cl.$^5$ .............................................. C09K 3/14
[52] U.S. Cl. ........................................ 51/298; 51/293; 51/307; 51/309; 433/166
[58] Field of Search ................. 51/293, 298, 307, 309; 433/166

[56] References Cited

U.S. PATENT DOCUMENTS

| | | | |
|---|---|---|---|
| 3,599,333 | 8/1971 | Muhler | 32/59 |
| 3,789,462 | 2/1974 | Reich | 32/59 |
| 3,964,166 | 6/1976 | Stahlman | 32/59 |
| 3,977,083 | 8/1976 | Leslie et al. | 32/58 |
| 3,977,084 | 8/1976 | Sloan | 32/59 |
| 4,055,897 | 11/1977 | Brix | 32/59 |
| 4,264,307 | 4/1981 | Neuwirth | 433/166 |
| 4,328,322 | 5/1982 | Baron | 521/163 |
| 4,381,792 | 5/1983 | Busch, Jr. et al. | 132/75.6 |
| 4,447,208 | 5/1984 | Kawai | 433/166 |
| 4,459,779 | 7/1984 | Shen | 51/296 |
| 4,636,171 | 1/1987 | Martis | 433/134 |
| 4,786,657 | 11/1988 | Hammer et al. | 522/90 |
| 5,078,754 | 1/1992 | Jefferies et al. | 51/298 |

OTHER PUBLICATIONS

*Thermal Plastic Elastomers, A Comprehensive Review*, Edited by M. R. Legge, G. Holden, and H. E. Schroeder, Hanser Publishers NY 1987, pp. 13–46.
Pfaltz & Bauer Catalog, 12th Edition, p. 272.

*Primary Examiner*—Mark L. Bell
*Assistant Examiner*—Willie J. Thompson
*Attorney, Agent, or Firm*—Gary L. Griswold; Walter N. Kirn; Jeffrey L. Wendt

[57] ABSTRACT

An abrasive composition and dental articles made from same, the composition including abrasive particles dispersed throughout and entrapped within a polyurea or polyurethane urea matrix which contains soft and hard segments wherein the matrix is made from the polymerization reaction of a polyfunctional amine and a polyfunctional isocyanate. The abrasive dental articles include prophylactic cups and polishing wheels, points and discs.

24 Claims, 1 Drawing Sheet

ABRASIVE DENTAL ARTICLES

This is a division of application Ser. No. 07/753,204 filed Aug. 30, 1991, now abandoned.

CROSS-REFERENCE TO RELATED APPLICATIONS

This application is related to assignee's copending U.S. application Ser. No. 07/753,225 filed Aug. 30, 1991.

BACKGROUND OF THE INVENTION

1. Field of the Invention

This invention relates generally to abrasive articles. More specifically, the invention relates to bonded abrasive dental articles comprising abrasive particles dispersed throughout and adhered within a polyurea or polyurethane urea matrix.

2. Description of Related Art

Abrasive dental articles comprising a solid or foamed polymeric matrix having abrasive particles dispersed throughout and bonded therein are known. The polymeric matrix may be a hard, thermoset resin, such as a catalyzed phenol-formaldehyde, or an elastomer, such as a polyurethane or a natural or synthetic rubber. Examples of abrasive dental articles comprising such polymeric idatrices can be found in U.S. Pat. Nos. 3,599,333, 3,964,166, 3,977,083, 4,381,792 and 4,636,17. Alternatively, an abrasive layer can be placed on a support or core. The support or core may be elastomeric as described in U.S. Pat. Nos. 3,977,084, 4,055,897 and 4,447,208 or nonelastomeric as described in U.S. Pat. No. 4,264,307.

U.S. Pat. No. 3,789,462 discloses a bonded abrasive dental article formed from a urethane elastomer which consists essentially of tolylene diisocyanate endcapped polytetrahydrofuran cured with 4,4'-methylene bis(o-chloroaniline) ("MOCA").

Bonded abrasives are to be distinguished from coated abrasives in their mode of operation. Bonded abrasives rely upon the continual breakdown and removal of the abrasive grains on the surface to continually present sharp cutting points to the material being ground. Coated abrasives, on the other hand, have only a single layer of abrasive grains. See, for example, U.S. Pat No. 5,011,5121, incorporated herein by reference.

While synthetic polymers comprising the reaction product of polyisocyanates and oligomeric aminobenzoic acid esters and amines and processes for their preparation are known, they have not been suggested for use as a binder for bonded abrasive articles. U.S. Pat. No. 4,328,322 describes such polymers and processes. The same is true for the polyurethanes and polyurethane/ureas crosslinked with 2-glyceryl acrylate or 2-glyceryl methacrylate which are disclosed in U.S. Pat. No. 4,786,657. This reference describes the use of high equivalent weight diols and diamines, 2-glyceryl (meth)acrylate, diisocyanates, and low equivalent weight glycols and amines in the production of the polyurethanes and polyurethane/ureas. (See also *Thermoplastic Elastomers, A Comprehensive Review*, edited by N. R. Legge, G. Holden and H. E. Schroeder, Hanser Publishers, New York, 1987, P. 13–46.)

SUMMARY OF THE INVENTION

The present invention provides bonded abrasive compositions and dental articles made from the compositions. In general, the compositions of the invention may be described as bonded abrasives suitable for use in abrasive dental articles, said compositions comprising:

(a) a cured binder matrix comprising a polyurea or polyurethane urea, said polyurea or polyurethane urea comprising the reaction product of a polyfunctional amine having an average active hydrogen functionality of about 2 and an equivalent weight of at least about 300, and a polyisocyanate comprising a polyfunctional isocyanate having an average functionality of at least about 2 and an equivalent weight of less than about 300, and (b) abrasive particles dispersed throughout said binder matrix.

Improved abrasive dental articles may be made using the abrasive compositions. The articles include abrasive-loaded dental devices suitable for being removably mounted on a dental handpiece, the devices including a shaped body of abrasive, elastomeric material containing abrasive particles dispersed throughout the elastomeric material, the shaped body being suitable for performing dental cleaning and polishing and having means for removably mounting the shaped body on a dental handpiece. The improved devices are made using the bonded abrasive compositions described herein.

The invention also provides a method of making bonded abrasive dental articles. The abrasive articles of the invention are preferably prepared by the following steps: (a) combining a polyfunctional amine having an average active hydrogen functionality of about 2 and an equivalent weight of at least about 300, a polyfunctional isocyanate having an average functionality of at least about 2 and an equivalent weight of less than about 300 and abrasive particles to form a mixture, and (b) curing the mixture.

The bonded abrasive compositions and articles made therefrom exhibit excellent cleaning and mechanical properties as evidenced by the Examples and disclosure provided hereinbelow. The abrasive articles of the invention, especially when fabricated into prophylactic cups, display good polishability and significantly lower rates of cup weight loss vis-a-vis conventional prophylactic cups.

DESCRIPTION OF PREFERRED EMBODIMENTS

Figure 1:
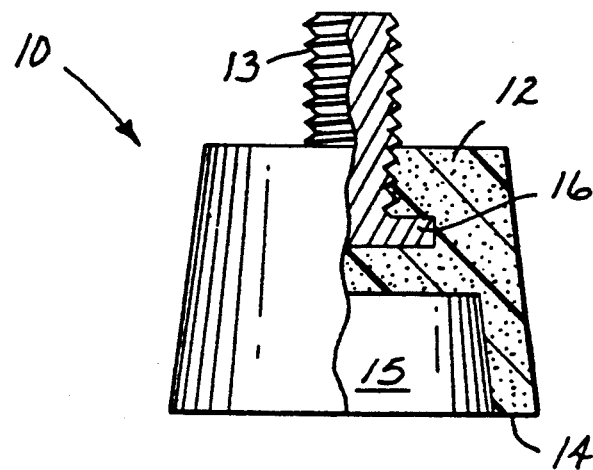
FIG. 1 is a view in elevation and partial section of a prophylactic cup made using the composition of the present invention.

As used herein, "soft segment" means a soft, flexible polymeric segment of the polyurea or polyurethane/urea which results from the polymerization of a polyfunctional amine having active hydrogen functionality of at least about 2 and an equivalent weight of at least about 300. The term "hard segment" means a harder, less flexible polymer segment which results from polymerization of (a) a polyfunctional isocyanate having a functionality of at least about 2 and equivalent weight of less than about 300, and (b) optional chain extender. "Chain extender" means low molecular weight (i.e., less than about 300) monomers having active hydrogen functionality, where "active hydrogen functionality" is used in its conventional sense to refer to the reactive hydroxy, amine, carboxyl and/or thiol groups present in a molecule. The individual soft segments associate to form soft regions in the binder while individual hard segments associate to form hard regions in the binder.

Bonded Abrasive Compositions

The bonded abrasive compositions of the invention are formed of abrasive particles dispersed throughout a polyurea or polyurethane urea binder matrix so as not to smear the binder matrix over the surfaces being abraded as the binder matrix gradually degrades under mechanical friction. The binder matrix comprises polyurea and polyurethane urea polymers having soft and hard segments where the polyurea or polyurethane urea is the reaction product of a polyfunctional amine and a polyfunctional isocyanate. Preferably there should be equal equivalents of active hydrogen atoms (i.e., amines plus alcohols) and isocyanates.

In the practice of this invention, it has been found that suitable binder matrices are selected from the group consisting of polyurea and polyurethane urea polymers which are the reaction product of a polyfunctional amine and a polyfunctional isocyanate, with the optional addition of a chain extender. These polyurea and polyurethane urea polymer binders are particularly well suited in that the resultant abrasive articles have sufficient integrity and abrasive particle retention (high efficiency) even at low binder matrix content. They are also substantially smear resistant (substantially no signs of the abrasive article remaining on the dental workpiece after the dental workpiece has been finished) when subjected to high revolutions per minute ("rpm") applications such as those frequently encountered in dental laboratory applications. It should be appreciated, however, that the compositions of the present invention can be formulated to increase the smearing when desired (for example, to create a surface finish on which dental plaque does not easily adhere).

Polyurea and polyurethane urea polymers especially well suited in the practice of this invention are made from polyfunctional amines which are oligomeric aromatic polyamines selected from the group consisting of:

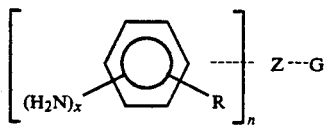

wherein n is an integer of from 2 to 4; each x is an integer of 1 or 2; each phenyl nucleus is para-amino, meta-amino, or di- metaamino substituted; each Z is

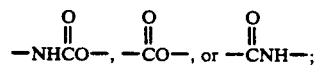

each R is hydrogen or lower alkyl, i.e., 4 carbon atoms or less; and G is an n-valent radical which may be obtained by the removal of hydroxyl or amino groups, respectively, from an n-valent polyol or polyamine having an equivalent weight of from about 300 to about 3000. Below an equivalent weight of about 300, it will be difficult to achieve the desired flexibility in the cured binder. On the other hand, an equivalent weight above about 3000 leads to shorter life of the abrasive article made using the polyamine, evidenced by average weight loss measurements (Example 11).

Preparation of oligomeric aromatic amines useful in the invention is described in detail in U.S. Pat. No. 4,328,322, incorporated herein by reference. Preferably the polyfunctional amines have an equivalent weight of at least about 300, and more preferably at least about 400. Examples of suitable polyfunctional amines include oligomeric aromatic amines commercially available from Air Products and Chemicals, Inc. under the tradenames POLAMINE 650, POLAMINE 1000, POLAMINE 1000G, POLAMINE 2000 and POLAMINE 2900. The numbering of the different polyfunctional amines known as POLAMINES indicates the approximate molecular weight, with one half of the number indicating the approximate equivalent weight.

The oligomeric aromatic amines are of two classes: aminobenzoic acid esters or amides where Z is

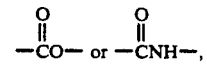

and aminophenyl urethanes where Z is

Preferably, the oligomeric aromatic polyamine is a substantially difunctional amino benzoic acid-terminated oligomer with a poly(tri-, tetra-, penta-, or hexa-)methylene ether backbone, having an equivalent weight ranging from about 300 to about 3000, or combinations thereof. Polytetramethylene ether backbone compositions are particularly preferable. Unlike assignee's copending application Ser. No. 07/753,205 filed concurrently with the present application (Bonded Abrasive Compositions and Articles Made Therefrom), the matrix binder can tolerate up to about 50 percent of the urea linkages substituted with urethane linkages as the length of service required of the abrasive articles of the present invention is much shorter than those of the copending application.

In certain applications up to about 80 percent of the polyfunctional amine may be substituted with polyfunctional alcohol having a functionality of about 2 and equivalent weight of at least about 300. Suitable polyfunctional alcohols are described in U.S. Pat. No. 4,786,657, columns 4-5, incorporated herein by reference. A particularly preferred polyfunctional alcohol is poly(tetramethylene) oxide, hydroxyl terminated, available from E.I. du Pont de Nemours & Co..

When employing oligomeric aromatic polyamines as the soft segment, the hard segments are polyfunctional isocyanates having an average functionality ranging from about 2.0 to about 4.0, and may be aliphatic, cycloaliphatic, arylaliphatic, aromatic, heterocyclic or mixtures thereof. The polyfunctional isocyanates preferably are aromatic or aliphatic polyisocyanates having an average functionality of at least about 2.0 and more preferably are aromatic polyisocyanates with a functionality ranging from about 2.0 to about 4.0, more preferably from about 2.0 to about 2.5. The polyfunctional isocyanate should be present in an amount sufficient to react with substantially all of the active hydrogen atoms in the polymerizable mixture, preferably the ratio of the active hydrogen atoms of the polyfunctional amines and the isocyanate groups of the polyfunctional isocyanate should range from about 0.95 to about 1.05, more preferably from about 0.99 to about 1.01.

Exemplary polyfunctional isocyanates include the polyisocyanate terminated reaction product of poly(tetramethylene glycol) polymer and an aromatic or aliphatic isocyanate having a functionality of at least about 2, or the reaction product of a dihydroxy terminated polyester such as poly(hexamethylene adipate) and an aromatic or aliphatic isocyanate having a functionality of at least about 2. Particularly preferable polyfunctional isocyanates include 1,6-hexamethylene diisocyanate, 1,4-cylcohexane diisocyanate, tolylene diisocyanate, p-phenyl diisocyanate, diphenylmethane diisocyanate, naphthylene-1,5diisocyanate, polymeric isocyanates, and mixtures thereof.

The polyfunctional isocyanates may be blocked with blocking agents that react with the isocyanate groups, a reaction that can be reversed at elevated temperatures to free the isocyanate groups which then can react with the polyfunctional amine. Examples of suitable polyfunctional blocked isocyanate polymers include those under the tradenames ADIPRENE BL90, ADIPRENE BL16 and ADIPRENE BL315, commercially available from Uniroyal Chemical Co., Inc. Preferably the abrasive articles made using the compositions of the invention are porous when employing blocked polyfunctional isocyanates so as to facilitate volatilization of the blocking agent.

Silane coupling agents can be added to the composition of the invention to provide higher modulus to the binder matrix and enhance structural integrity. Suitable silane coupling agents include epoxy silanes, mercapto silanes, acrylato silanes, methacrylato silanes and mixtures thereof. Particularly preferred silanes are epoxy silanes such as gamma-glycidoxypropyltrimethoxysilane and 3,4-epoxycyclohexylmethyltrimethoxysilane.

Where polyurea and polyurethane urea polymers are made from oligomeric aromatic polyamine soft segments and polyfunctional isocyanate hard segments, the polyurea and polyurethane urea polymers may contain chain extenders. The chain extenders preferably have an active hydrogen functionality from about 2 to 8, preferably from about 2 to 4, and more preferably from about 2 to 3, and an equivalent weight less than about 300, preferably less than 200. Well suited chain extenders are low molecular weight polyfunctional amines including aromatic, alkylaromatic, or alkyl polyfunctional amines, preferably primary amines. Examples of low molecular weight polyfunctional aromatic amines include methylene dianiline ("MDA"), polymeric methylene dianilines having a functionality of 2.1 to 4.0 which include the dianiline CURITHANE 103, commercially available from Dow Chemical Company, and the dianiline MDA-85, from Bayer Corporation. The dianiline CURITHANE 103 has an average amine functionality of about 2.3 and is composed of 65% 4,4'-methylene dianiline, 5% 2,4'-methylene dianiline, and 30% polymeric methylene dianiline. The dianiline MDA-85 contains about 85% 4,4'-methylene dianiline and 15% polymeric methylene dianiline and amine functionality of about 2.2.

Examples of other suitable amine chain extenders include ethylene diamine, 1,5-diamine-2-methyl pentane, and tris(2-aminoethyl) amine. Other suitable chain extenders include trimethylolpropane monoalkyl ether, ethanolamine, diethanolamine, methylene dianiline, diethyl toluene diamine, 2-methylpentamethylenediamine, para-phenylenediamine, ethylene glycol, propylene glycol (1,2 and 1,3), butylene glycol (1,4 and 2,3), 1,4 butenediol, 1,4 butanediol, various hydroxy substitutions of pentanediol, hexanediol and octanediol, trimethylolpropane, and mixtures thereof.

Conventional abrasive particles can be employed in the abrasive compositions of the invention and for compositions formulated into dental articles to be used primarily in dental operatory applications, particles or agglomerates of small size are preferred. However, when the compositions are formed into wheels especially for use in the dental laboratory, preformed agglomerates of abrasive particles are useful because the resultant abrasive articles have high rates of abrasion, yet produce a smooth surface finish. Voids in the formed article are acceptable, but preferably should be small in number and size.

The abrasive particles used to produce the abrasive dental articles of the invention may be particles or agglomerates of small particles. The abrasive particles may be of any known abrasive material commonly used in the abrasive art. Examples of suitable abrasive particles include silicon carbide (including refractory coated silicon carbide (such as disclosed in U.S. Pat. No. 4,505,720), aluminum oxide, alumina zirconia (including fused alumina zirconia such as disclosed in U.S. Pat. Nos. 3,781,172, 3,891,408, and 3,893,826, commercially available from the Norton Company of Worcester, Mass., under the trade designation NORZON), cubic boron nitride, garnet, pumice, sand, emery, mica, corundum, quartz, diamond, boron carbide, fused alumina, calcined alpha alumina, sintered alumina, alpha alumina-based ceramic material (available from Minnesota Mining and Manufacturing Company under the trade designation CUBITRON), as disclosed in U.S. Pat. Nos. 4,314,827, 4,518,397, 4,574,003, 4,623,364, 4,744,802, and EP publication 228,856, and combinations thereof. The preferred abrasives are pumice and alumina. When pumice is used, it is preferred that it range in grade from about 4F to 2 with 4F to 1 being more preferred. When using alumina, fused alumina and calcined alpha alumina having a particle size in the range of about 1 to 125 microns are preferred. The grade and type of abrasive particles used are selected so as to produce the desired abrasion and surface finish.

Bonded Abrasive Dental Articles

Figure 2:
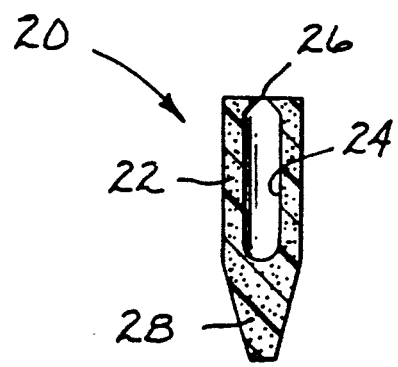
FIG. 2 is a cross-sectional view of a polishing tip made using the composition of the present invention.
Figure 3:
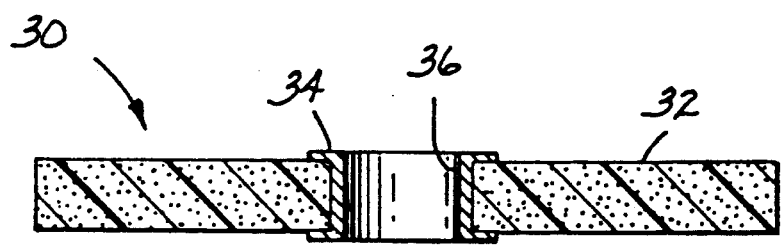
FIG. 3 shows a cross-sectional view of a disc-shaped abrasive article made using the composition of the present invention.

Abrasive dental articles made using compositions of the invention can be used to clean and polish teeth or dental resins, composites, porcelains, amalgams or precious and semiprecious metals. These abrasive dental articles may be formulated into a variety of conventional forms as shown in FIGS. 1-3, such as polishing cups (i.e., prophylactic cups or phrophy cups) having fluted or unfluted auxilliary application means, and polishing points, discs and cylinders. When fabricated into a dental prophylactic cup, the article will remove plaque and stains left on the teeth after routine brushing and will provide high luster and smooth polish to the teeth.

FIG. 1 shows an abrasive prophylactic cup 10 made using the composition of the present invention, cup 10 formed from an abrasive-filled elastomeric material 12 as described herein. The elastomeric material has sufficient flexibility so that when pressure is applied to cup 10 edge 14 will deform to form a lip, that is, edge 14 does not roll under but spreads and rolls outwardly so the interior surface 15 of the cup contacts the surface to be cleaned, and the edge is also available for cleaning subgingival areas. The cup has means 13, here a threaded stud, for attachment to a dental handpiece (not shown). The threaded stud is anchored in the elastomeric material by means of a head 16.

FIG. 2 shows another embodiment of an abrasive article (a polishing tip 20) made using the composition of the present invention. Polishing tip 20 includes a body portion 22 which has a hollow cylindrical interior 24 having a diameter and length substantially equal to those of a working piece of a mandrel (not shown). The body portion 22 of polishing tip 20 also includes a reduced diameter aperture 26 extending from and coaxial with the hollow interior 24 and opening to the external surface of the body portion. Polishing tip 20 also includes an end portion 28 which is conical in FIG. 2 but which may assume a variety of shapes such as ball-shaped, cup-shaped, or other varieties, limited only by the requirement that there be sufficient material present to withstand the forces generated by rotation.

FIG. 3 shows a third embodiment of an abrasive article (an abrasive disc 30) made using the composition of the present invention. Disc 30 includes an annular piece 32 made of the composition above-described, varying from about 3 mm to about 50 mm in height and from about 0.5 cm to about 1 cm in diameter. The larger articles are generally used by dental laboratories, whereas the smaller articles are generally used in the dental operatory. An attachment means 34 for attaching disc 30 to a driving means (e.,g., a mandrel) is also provided. In the embodiment shown in FIG. 3 attachment means 34 comprises an opening through disc 30. A hub 36 is provided around attachment means 34 and reinforces those portions of disc 30 which define attachment means 34.

As shown with reference to FIG. 3, the articles of the invention typically have a central opening for mounting on an appropriate arbor or other mechanical holding means to enable the article to rotate in use. Further, these abrasive dental articles may be formed into an annulus which may be adhered to a backing, such as a metal or plastic disc. Also the abrasive article may be applied to and secured to a flexible backing such as plastic, cloth and the like. The bond system which binds the abrasive compositions to the backing may be the same or different from the polyurea binder or the bond system holding aggregate particles together. Article dimensions, configurations, means of support, and means of rotation are well-known in the art. When the articles are in the form of wheels, they are typically in the form of a right cylinder varying from about 3 mm to about 2 cm in height and from about 3 mm to about 1 cm in diameter.

Abrasive articles made with individual abrasive particles preferably do not contain voids and preferably contain about 10 to 90 weight percent abrasive, more preferably about 40 to 70 percent abrasive and most preferably about 40 to 60 percent abrasive. Preferably abrasive particles range is size from about 1 to 500 microns and more preferably from about 3 to 250 microns. Agglomerates are particularly preferred for polishing wheels for use in the dental laboratory. Preferably, the agglomerates range in size from about 3 to about 300 microns.

Optionally, organic or inorganic fluoride sources, lubricants, grinding aids, coupling agents, plasticizers, diluents, fillers, reinforcing fibers, fillers, flavorants, viscosity modifiers, coloring agents and process aids and other ingredients that will be apparent to those skilled in the art may be added to the polymerizable mixture as desired.

Method of Making Bonded Abrasive Dental Articles

The bonded abrasive dental articles of the present invention can be made by a variety of methods depending on the shape of the article to be formed and whether a backing is utilized. The abrasive particle-liquid mixture can be cast molded, transfer molded, liquid injection molded, reaction injection molded or molded using other techniques well known to those skilled in the art. The preferred method of forming dental articles is transfer molding. In general, this method may be described in two steps: (a) combining a polyfunctional amine and polyfunctional isocyanate as those reactants are above described and a sufficient amount of abrasive particles to form a curable abrasive mixture; and (b) curing the mixture to form the bonded abrasive dental article. Exemplary methods include those methods wherein the curable mixture is introduced into a mold prior to curing, those methods where the mixture is applied to a backing before curing, and methods wherein the polyfunctional amine is an oligomeric aromatic polyfunctional amine as above described.

Preferred embodiments of the method include those methods wherein the polyfunctional isocyanate is an aromatic polyisocyanate having a functionality ranging from about 2.0 to about 2.5, and wherein said abrasive particles are selected from the group consisting of pumice and alumina, the alumina selected from the group consisting of fused alumina, calcined alpha alumina, sintered alumina, alpha alumina-based ceramic material, and combinations of these. Still more preferred are those methods wherein chain extenders, as described herein above, are added to the mixture.

The invention is further illustrated by the following nonlimiting examples where all parts and percentages are by weight unless otherwise specified. Although good results are generally achieved without commercially available prophylactic pastes, these pastes can be used with the articles made from the compositions of the invention in particularly difficult applications. These examples should not be interpreted as literally limiting the scope of the invention.

EXAMPLES

Example 1

Abrasive filled (44.9%) polyurea dental prophylactic cups were prepared by placing 5.2 parts of a polytetramethyleneoxide-di-p-aminobenzoate having an average molecular weight of about 2000 and an equivalent weight of about 1000 known as POLYAMINE 2000, Air Products and Chemicals, Inc., in a vessel and heating to 50° C. 0.65 part of an aromatic polymeric isocyanate having an equivalent weight of 130 known as MONDUR MRS-4, Mobay Chemical Company, 0.05 part of an epoxy silane coupling agent known as Z-6040, Dow Corning, and 4.8 parts medium pumice (grade 0 ½, Lot 524, Moyco Industries, Inc.) were added and the resulting mixture hand spatulated for about 3 minutes. The mixture was then degassed by applying a vacuum at about 10 mm Hg and then releasing to atmospheric pressure. This process was repeated two or three times. Two types of prophylactic cup mold assemblies were used, snap-on type and screw-on type. Each type of mold base had four cylindrical tapered cavities that were 8 mm high, 5 mm in diameter on the edge that was to be attached to the dental instrument and 6 mm in diameter on the edge that was to form a lip for cleaning. The snap-on type mold base was fabricated with a peg at the bottom of the mold. The screw-on type mold base had a depression at the bottom of each cavity for placement of a screw prior to adding the mixture. The mixture was hand spatulated into each of the types of mold bases and covered with a mold lid that had spikes corresponding to each cup cavity to form the center of the cup. The mold lid was clamped onto the mold base with a C-clamp. The mold assemblies were placed in a 100° C. oven for 1 hour, removed from the oven and allowed to cool to room temperature. The cups were removed from the mold assemblies and evaluated in the laboratory for cleaning efficiency and mechanical strength and in patients for clinical efficacy.

Cups were laboratory tested for cleaning efficiency by spinning the formed cup against a lacquered metal surface at 1800 rpm with an impressed load of about 450 g while the metal and cup were immersed in room temperature water. The lacquer was 0.013 mm thick and had a 4H pencil hardness. The cleaning efficiency results were evaluated in terms of lacquer removal and reported as a (+) if the lacquer was removed in 30 seconds or less and as a (−) if lacquer remained after 30 seconds. The lacquer removal results for two cups of the formulation were (+,+). The removal rate of lacquer was equated with in vivo cleaning through clinical evaluation of cups having the same composition as the laboratory tested cups. This was found to be adequate based on clinical tests that showed that cups of this formulation would clean one entire mouth of moderately stained teeth.

Commonly used prophylactic paste, Nupro Dental Prophy Paste (Janar and Co.), in combination with a commercially available prophylactic cup, Patterson Centra 6-WEB (screw-on type cup, Patterson Dental Company), was used under the same laboratory conditions as the cups of the invention. The prophy cup with paste removed the lacquer in approximately 15 seconds. However, when the two prophy cups commercially known as Patterson Centra 6-WEB cups were laboratory tested without using prophy paste, lacquer remained on the metal surface after 30 seconds and the cups were rated as (−,−).

Cups were laboratory tested for mechanical strength by spinning the formed cup at 1800 rpm on a 400 grit silicon carbide paper under a load of about 450 g for 90 seconds. The mechanical strength was evaluated in terms of weight loss and was determined by weighing the cup before and after testing, dividing the difference between the before/after weight by the before weight and multiplying by 100 to give the percent weight loss. Two cups of the formulation were tested for mechanical strength and the average weight loss was 2.5%. As a control, two prophy cups commercially known as Patterson Centra 6-WEB cups without prophy paste were similarly evaluated for mechanical strength and showed about 12% weight loss. The cups were also visually checked at 30, 60 and 90 second intervals for tearing, loss of lip formation and general disintegration. The cups of the invention exhibited retention of lip integrity, whereas the prophy cups commercially known as Patterson Centra 6-WEB cups showed uneven wear and tearing of the lip. Cups showing visual degeneration in less than 90 seconds were considered less desirable and probably would not clean one entire mouth of moderately stained teeth. However, cups that will not withstand 90 seconds of this test would be suitable for use on mildly stained teeth. Moreover, more than one cup can be used for cleaning a single mouth.

About 12 snap-on type cups and about 50 screw-on type cups of the above formulation were clinically evaluated by 5 dentists, 3 dental assistants and 3 dental hygienists. On slightly and moderately stained teeth, one cup was sufficient to clean an entire mouth. On severely stained teeth, occasionally a second cup was required. Both clinicians and patients reported that the procedure was completed in less time, required less rinsing of the mouth to remove abrasive particles and loosened plaque, and was neater insofar as no paste was used. The clinicians also reported better visibility, less spray and cleaning equal to currently used commercially available cups with paste. The patients reported less discomfort with grit and paste in the mouth and teeth feeling smoother and cleaner than after previous cleanings.

Example 2

The formulation of EXAMPLE 1 was repeated with the addition of 0.100 part of the flavor known by the trademark POWDERED POLYIF MINT 1403 (International Flavor and Fragrance, Inc.) and 0.1 part powdered sodium fluoride (Mallinckrodt Chemical Works). The mixture was hand spatulated, degassed and molded into screw-on type cups as described in EXAMPLE 1.

To evaluate fluoride release, one cup was placed in a vessel containing approximately 10 ml of distilled water at room temperature for one hour. The cup was removed from the vessel and the fluoride content in the water measured using an Orion Accumet 950 ph/ion meter with a fluoride selective electrode, Orion Model 960900 (both from Orion Research Inc., Cambridge, MA). The electrode was calibrated using fluoride solutions of concentrations equivalent to Fluoride Activity Standards #940907 and #040908, standard fluids of 100 parts per million ("ppm") fluoride ion and 10 ppm fluoride ion respectively (both available from Orion Research Inc.). The fluoride ion concentration reading in ppm was multiplied by the volume of solution to provide the amount of fluoride released in micrograms. one cup of the same formulation without the incorporation of a fluoride source and one commercially available prophylactic cup known as the EZ E-35 Prophy Cup (EZ, Kirkland, WA) were similarly tested for fluoride release. The fluoride release results are set out in TABLE I.

TABLE I

| Cup Type | Fluoride Released (Micrograms) |
|---|---|
| With Fluoride Source | 21 |
| Without Fluoride Source | 0 |
| EZ E-35 Prophy Cup | 0 |

In addition, one cup was tested under simulated clinical conditions to measure fluoride release. The cup was mounted on a dental handpiece normally used during a regular dental prophylactic cleaning. The cup was rotated on an extracted human tooth for 30 seconds, after which time the tooth and cup were rinsed with 10 drops of distilled water. This procedure was repeated 20 times with the water from each rinse combined and fluoride release measured as described above. One cup of the same formulation without the incorporation of a fluoride source and one EZ E-35 Prophy Cup were similarly tested for fluoride release. The fluoride release results are set out in TABLE II.

TABLE II

| Cup Type | Fluoride Released (Micrograms) |
| --- | --- |
| With fluoride Source | 19 |
| Without Fluoride Source | 1 |
| EZ E-35 Prophy Cup | 0.5 |

The data of TABLES I and II show that fluoride was released under laboratory conditions and simulated clinical conditions by the cup of the invention that had a fluoride source incorporated therein with very little or no fluoride released by the same cup of the invention without a fluoride source incorporated therein or a commercially available prophy cup.

Example 3

Dental prophylactic cups were prepared with varying percentages of medium pumice using the formulation and method detailed in EXAMPLE 1, but with different amounts of pumice. Each formulation was molded into four screw-on type prophylactic cups and laboratory tested for cleaning efficiency and mechanical strength according to EXAMPLE 1.

Set out below in TABLE III are the amount of pumice, the cleaning efficiency in terms of "Lacquer Removal" and the mechanical strength in terms of "Weight Loss". As a "Control" two EZ E-35 Prophy Cups were tested with no prophy paste. For each run the mechanical strength results of two samples was averaged.

TABLE III

| Run no. | Pumice Amount (%) | Lacquer Removal (+,−) | Weight Loss (%) |
| --- | --- | --- | --- |
| Control | 0 | −,− | 16.0 |
| 1 | 0 | −,− | 14.3 |
| 2 | 14.5 | +,+ | 7.9 |
| 3 | 25.3 | +,+ | 2.6 |
| 4 | 33.7 | +,+ | 2.6 |
| 5 | 50.4 | +,+ | 3.3 |

The data show that the polyurea prophylactic cups of the invention that contain abrasive have good cleaning efficiency and low weight loss compared to either a similar polyurea cup without abrasive or a commercially available cup used without prophy paste.

Example 4

Dental prophylactic cups were prepared using the formulation and method detailed in EXAMPLE 1, but with three size ranges of silicon carbide agglomerates instead of the medium pumice. The silicon carbide agglomerates were simultaneously sieved through a 250 and a 180 mesh screen to provide the agglomerate sizes listed in TABLE IV. Each formulation was molded into four screw-on type prophylactic cups and laboratory tested for cleaning efficiency and mechanical strength according to EXAMPLE 1.

Set out below in TABLE IV are the agglomerate size, the cleaning efficiency in terms of lacquer removal and the mechanical strength in terms of weight loss. The mechanical strength for two samples of each run was averaged.

TABLE IV

| Run no. | Agglom. Size (Mesh) | Lacquer Rem. (+,−) | Weight Loss (%) |
| --- | --- | --- | --- |
| 1 | >180 | +,+ | 1.8 |
| 2 | 180-250 | +,+ | 1.0 |
| 3 | <250 | +,+ | 1.0 |

The data show that agglomerates incorporated into the polyurea prophylactic cups of the invention provide good cleaning efficiency and low weight loss.

Example 5

The formulation of EXAMPLE 1 was repeated, substituting a polytetramethyleneoxide-di-p-aminobenzoate having an average molecular weight of about 1240 and an equivalent weight of about 620 known as POLYAMINE 1000G, Air Products and Chemicals, Inc., 2.39 parts, and a polytetramethyleneoxide-di-p-aminobenzoate having an average molecular weight of about 650 and an equivalent weight of about 375 known as POLYAMINE 650, Air Products and Chemicals, Inc., 2.5 parts, independently for the aminobenzoate known as POLAMINE 2000, and 3.0 parts medium pumice were used instead of 4.8 parts. Each mixture was prepared, degassed, molded into four screw-on type cups and tested as described in EXAMPLE 1.

For the run in which the aminobenzoate POLAMINE 1000 G was substituted for the aminobenzoate known as POLAMINE 2000, the cleaning efficiency in terms of lacquer removal was (+,+) and the average mechanical strength in terms of weight loss was 2.4% and when the aminobenzoate POLAMINE 650 was substituted for the aminobenzoate POLAMINE 2000, the lacquer removal was (+,+) and the average weight loss was 2.1%.

The testing results show that the aminobenzoates POLAMINE 1000 G and POLAMINE 650 can be used to make cups that exhibit comparable cleaning efficiency and mechanical strength properties to those made with the aminobenzoate POLAMINE 2000.

Example 6

Dental prophylactic cups were prepared using the formulation and method detailed in EXAMPLE 1, but with isocyanates other than the isocyanate MONDUR MRS-4. Each formulation was molded into four screw-on type cups and laboratory tested for cleaning efficiency and mechanical strength according to EXAMPLE 1.

Set out below in TABLE V are the type and amount of isocyanate and the cleaning efficiency in terms of lacquer removal and the mechanical strength in terms of weight loss. The mechanical strength results for two samples of each run were averaged.

TABLE V

| Run no. | Isocyanate Type, Amount (Parts) | Lacquer Rem. (+,−) | Wt. Loss (%) |
| --- | --- | --- | --- |
| 1 | PAPI 94[1], 0.66 | +,+ | 1.9 |
| 2 | PAPI 2020[2], 0.69 | +,+ | 1.4 |
| 3 | PAPI 2027[3], 0.67 | +,+ | 2.8 |
| 4 | ISONATE 143L[4], 0.72 | +,+ | 4.2 |
| 5 | RUBINATE M[5], 0.67 | +,+ | 1.6 |
| 6 | MONDUR CD[6], 0.72 | +,+ | 6.2 |
| 7 | MONDUR MR 200[7], 0.68 | +,+ | 1.8 |

TABLE V-continued

| Run no. | Isocyanate Type, Amount (Parts) | Lacquer Rem. (+,−) | Wt. Loss (%) |
|---|---|---|---|
| 8 | MONDUR MR[8], 0.66 | +,+ | 2.4 |

[1] A polymeric methylene diphenyl diisocyanate ("MDI") with a functionality of 2.3 and an equivalent weight of 131, Dow Chemical Company (PAPI is a trademark).
[2] A polymeric MDI with a functionality of 3.2 and an equivalent weight of 138, Dow Chemical Company (PAPI is a trademark).
[3] A polymeric MDI with a functionality of 2.7 and an equivalent weight of 134, Dow Chemical Company (PAPI is a trademark).
[4] A polymeric MDI with a functionality of 2.1 and an equivalent weight of about 145, Dow Chemical Company (ISONATE is a trademark).
[5] A polymeric MDI with a functionality of 2.7 and an equivalent weight of 133, Imperial Chemical Industries (RUBINATE is a trademark).
[6] A modified aromatic diisocyanate with an equivalent weight of 143 and containing 29.3% isocyanate groups, Mobay Chemical Company (MONDUR is a trademark).
[7] A polymeric diphenylmethane diisocyanate with an equivalent weight of 135, Mobay Chemical Company (MONDUR is a trademark).
[8] A polymeric diphenylmethane diisocyanate with an equivalent weight of 132, Mobay Chemical Company (MONDUR is a trademark).

The data show that various isocyanate hard segments can be incorporated into the polyurea prophylactic cups of the invention and provide good cleaning efficiency and low weight loss. While cups of all runs showed good cleaning efficiency and mechanical strength results, the cups of run nos. 1, 2, 5 and 7 exhibited very low weight loss.

Example 7

Abrasive filled polyurethane urea dental prophylactic cups were prepared as in Example 1 but by substituting various amounts of poly(tetramethylene)oxide (PTMO), a hydroxyl terminated polyoxide with a number average molecular weight of about 1000, available from E.I. du Pont de Nemours & Co., for the polyfunctional amine. The various ingredients are summarized in Table VI, with efficiency and weight loss indicated. Further tests were made using about 900 g force rather than about 450 g force at 1800 rpm against 400 grit sandpaper. These results are shown in Table VII.

TABLE VI[1]

| Run | Parts Amine[5] | Parts PTMO | Parts Isocyanate[4] | Parts Pumice[3] | Efficiency | Wt. Loss (%)[2] |
|---|---|---|---|---|---|---|
| Ex. 1 | 5.2 | 0 | 0.65 | 4.8 | (+) | 2.5 |
| 7a | 0 | 5.0 | 1 | 6.3 | (+) | 6.3 |
| 7b | 2.6 | 5.0 | 1.63 | 9.2 | (+) | 2.0 |
| 7c | 5.2 | 5.0 | 1.63 | 12.0 | (+) | 2.0 |

[1] All tests utilized 0.1 part silane coupling agent z-6040 except Example 1.
[2] Measured according to Example 1.
[3] Medium pumice, grade 0 ½, Lot 524, Moyco Industries, Inc.
[4] MONDUR MRS-4, Mobay Chemical Company
[5] POLYAMINE 2000, Air Products and Chemicals, Inc.

TABLE VII

| Material | Initial Weight | Wt. After 30 sec. | % Wt. Loss |
|---|---|---|---|
| Example 1 | 0.4164 gm | 0.4129 | 0.8 |
| 7a | 0.4017 | 0.3444[1] | 14 |
| 7b | 0.3993 | 0.3908 | 2 |
| 7c | 0.4122 | 0.4039[2] | 2 |

[1] no lip left.
[2] lip torn.

The 900 g weight shows much clearer difference between compositions containing 100% urethane linkages versus the compositions having predominantly urea linkages. The results show that cups with good cleaning efficiency and mechanical strength can be made with a formulation substituting a polyfunctional alcohol for the polyfunctional amine, in amounts approaching 80% substitution.

Example 8

Abrasive filled polyurethane urea dental prophylactic cups were prepared by placing 10.4 parts of the aminobenzoate POLAMINE 2000 in a vessel and heating to 50° C. 2.64 Parts of the isocyanate MONDUR MRS-4, 0.10 part of epoxy silane coupling agent Z-6040, 0.45 part 1,4-butanediol (chain extender, Aldrich Chemical Co., Inc.) and 9.6 parts medium pumice(grade 0 ½, Lot 524, Moyco Industries, Inc.) were added and the resulting mixture hand spatulated in a vessel for about 3 minutes. The mixture was degassed, placed in screw-on type molds, heated in an oven, removed and tested as detailed in EXAMPLE 7, except that the time in the oven was 2 hours instead of overnight.

Four cups were tested for cleaning efficiency and mechanical strength as detailed in EXAMPLE 1. The cleaning efficiency was (+,+) and the average weight loss was 3.0%. The results show that cups with good cleaning efficiency and mechanical strength can be made with a formulation incorporating a low equivalent weight glycol chain extender.

Example 9

The formulation of EXAMPLE 8 was repeated, except that 1.02 part of a mixture of 70% methylene dianiline and 304 polymeric methylene dianiline with a functionality of about 2.3 and an equivalent weight of about 101 known as CURITHANE 103, Dow Chemical Company, was substituted for 1,4-butanediol. The dianiline was dissolved in the aminobenzoate known as POLAMINE 2000 and the remaining ingredients added. The resultant mixture was hand spatulated, degassed and molded into screw-on type cups as detailed in EXAMPLE 7.

Four cups were tested for cleaning efficiency and mechanical strength as detailed in EXAMPLE 1. The cleaning efficiency was (+,+) and the average weight loss was 3.1%. The results show that cups with good cleaning efficiency and mechanical strength can be made with a formulation incorporating a low equivalent weight diamine chain extender.

Example 10

Abrasive filled polyurea dental prophylactic cups were prepared by placing 5.2 parts of the aminobenzoate known as POLAMINE 2000 in a vessel and heating to 50° C. 0.66 Part of the isocyanate MONDUR MR, 0.05 part of epoxy silane coupling agent Z-6040, 0.10 part GREEN LAKE BLEND #09236 (green dye, Warner Jenkinson, Lot 1128G) and 4.8 parts medium pumice (grade 0 ½, Lot 524, Moyco Industries, Inc.) were added and the resulting mixture hand spatulated for about 3 minutes. The mixture was degassed, molded into both snap-on type and screw-on type cups as described in EXAMPLE 1. This shows that cups of the invention can be made with the incorporation of a dye to provide uniformly colored cups.

Example 11

Abrasive filled polyurea dental prophylactic cups were prepared by placing 6.85 parts of the aminobenzoate POLAMINE 2900 (a polytetramethyleneoxide-di-p-aminobenzoate having an average molecular weight of about 2900 and an equivalent weight of about 1400, Air Products and Chemicals, Inc.) in a vessel and heating to 50° C. 0.72 Part of the isocyanate MONDUR CD, 0.05 part of epoxy silane coupling agent Z-6040, 0.05 part oleic acid (condensation catalyst, Sigma Chemical Co.) and 4.8 parts medium pumice (grade 0 ½, Lot 524, Moyco Industries, Inc.) were added. The resultant mixture was hand spatulated, degassed and molded into screw-on type cups.

Four cups were tested for cleaning efficiency and mechanical strength as detailed in EXAMPLE 1. The cleaning efficiency was (−,−) and the average weight loss was 6.4%. However, when an impressed load of about 680–900 g was used, the cleaning efficiency was (+,+). The results show that cups can be made using the aminobenzoate POLAMINE 2900, but their cleaning efficiency and mechanical strength properties are marginally acceptable. However, these cups could be used to clean mildly stained teeth and more than one cup may be required to clean an entire mouth. Also, the hard segment content could be increased by adding a chain extender and additional isocyanate to make a more durable cup.

Example 12

The formulation of EXAMPLE 1 was repeated using 4.8 parts of 30 micron calcined white alpha alumina (Abrasive Systems Division, Minnesota Mining and Manufacturing company, St. Paul, Minnesota) instead of medium pumice. The mixture was hand spatulated and degassed as detailed in EXAMPLE 1. The mixture was spread into a thin film (about 1-2 mm thick) and cured as described in EXAMPLE 1. A disc of about 1 cm in diameter was cut out and mounted on a dental drill using a screw holder. The disk was used to polish a 20 mm × 6 mm × 3 mm plug of cured dental composite made using the restorative known as SILUX PLUS Light Cure Restorative (No. 5702U, Minnesota Mining and Manufacturing Company, St. Paul, Minnesota). The surface of the composite plug was roughened with a medium contouring disk known as the SOF-LEX Contouring and Polishing Disc (Minnesota Mining and Manufacturing Company, St. Paul, Minnesota). The disc of the invention provided a smooth polished surface gloss comparable to that using a series of discs known as SOF-LEX ranging from fine to superfine.

Example 13

The formulation of EXAMPLE 12 was spatulated into a mold to make a polishing point. The mold was 12 mm long and 5 mm in diameter with the polishing end tapered and a central cavity for attachment to a snap-on type dental handpiece. The mixture was cured as described in EXAMPLE 1. The polishing point was then used to polish a roughened composite plug made using the restorative SILUX PLUS Light Cure Restorative as described in EXAMPLE 12. The polishing point of the invention provided a smooth polished finish.

Although this invention has been described using certain illustrative examples, it should be understood that the invention is not limited to the specific exemplary embodiments shown in this specification. For example, differing amounts of abrasive may be required in certain applications than in others and with different combinations of polyamine soft segment/polyisocyanate hard segment combinations to achieve the desired results.

What is claimed is:

1. A bonded abrasive composition suitable for use in abrasive dental articles, said composition comprising:
   (a) a cured binder matrix comprising a polyurea or polyurethane urea, said polyurea or polyurethane urea comprising the reaction product of a polyfunctional amine having an average active hydrogen functionality of about 2 and an equivalent weight of at least about 300, and a polyisocyanate comprising a polyfunctional isocyanate having an average functionality of at least about 2 and an equivalent weight of less than about 300, and
   (b) abrasive particles dispersed throughout said binder matrix.

2. A bonded abrasive composition in accordance with claim 1 wherein up to about 80 percent of the polyfunctional amine is substituted with a polyfunctional alcohol having active hydrogen functionality of at least and an equivalent weight of at least about 300.

3. A bonded abrasive composition in accordance with claim 1, wherein the polyfunctional amine is an oligomeric aromatic polyfunctional amine selected from the group consisting of:

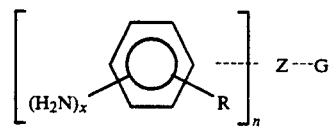

wherein n is an integer ranging from about 2 to about 4; each x is an integer ranging from about 1 to about 2; each phenyl nucleus is para-amino, meta-amino, or di-meta-amino substituted; each Z is selected from the group consisting of

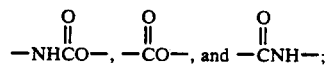

each R is hydrogen or lower alkyl of about 4 carbon atoms or less; and G is an n-valent radical which may be obtained by the removal of hydroxyl or amino groups, respectively, from an n-valent polyol or polyamine having an equivalent weight ranging from about 300 to about 3000.

4. A bonded abrasive composition in accordance with claim 3, wherein the oligomeric aromatic polyfunctional amine has an equivalent weight of at least about 400.

5. A bonded abrasive composition in accordance with claim 1, wherein the polyfunctional isocyanate has a functionality ranging from about 2.0 to about 2.5 and has an equivalent weight of at least about 30.

6. A bonded abrasive composition in accordance with claim 1, further comprising a chain extender having an active hydrogen functionality ranging from about 2 to about 8 and an equivalent weight less than about 300.

7. A bonded abrasive composition in accordance with claim 1, wherein the abrasive particles are present in an amount from about 10 to about 90 weight percent.

8. A bonded abrasive composition in accordance with claim 1, wherein the abrasive particles are selected from the group consisting of pumice and alumina, the alumina selected from the group consisting of fused alumina, sintered alumina, calcined alpha alumina, alpha alumina-based ceramic material, and mixtures of these.

9. A bonded abrasive composition in accordance with claim 8, wherein the pumice ranges in grade from about grade 4F to about 1.

10. A bonded abrasive composition in accordance with claim 8, wherein the alumina has a particle size ranging from about 3 to about 250 microns.

11. A bonded abrasive composition in accordance with claim 1, wherein the abrasive particles comprise agglomerates ranging in size from about 3 to about 300 microns.

12. A bonded abrasive composition in accordance with claim 1, further comprising an organic or inorganic fluoride source.

13. A bonded abrasive composition in accordance with claim 1, further comprising a silane coupling agent.

14. In a bonded abrasive-loaded dental cleaning and polishing device suitable for being removably mounted on a dental handpiece, comprising a shaped body of abrasive, elastomeric material containing abrasive particles dispersed throughout the elastomeric material, said shaped body being suitable for performing dental cleaning and polishing having means for removably mounting said shaped body on a dental handpiece, the improvement which comprises using as said elastomeric material a binder matrix comprising a polyurea or polyurethane urea, said polyurea or polyurethane urea comprising the reaction product of a polyfunctional amine having an average active hydrogen functionality of about 2 and an equivalent weight of at least about 300, and a polyisocyanate comprising a polyfunctional isocyanate having an average functionality of at least about 2 and an equivalent weight of less than about 300, and abrasive particles dispersed throughout said binder matrix.

15. A cleaning and polishing device in accordance with claim 14, wherein said shaped body is a dental prophylactic cup.

16. A cleaning and polishing device in accordance with claim 14, wherein said shaped body is a polishing wheel.

17. A cleaning and polishing device in accordance with claim 14, wherein said shaped body is a polishing point.

18. A cleaning and polishing device in accordance with claim 14, wherein said shaped body is a polishing disc.

19. A method of making a bonded abrasive dental article, said method comprising:
(a) combining a polyfunctional amine having an average active hydrogen functionality of about 2 and an equivalent weight of at least about 300, a polyfunctional isocyanate having an average functionality of at least about 2 and an equivalent weight of less than about 300, and a sufficient amount of abrasive particles to form a curable abrasive mixture; and
(b) curing the mixture to form said bonded abrasive dental article.

20. A method in accordance with claim 19 which further comprises introducing said curable abrasive mixture into a mold prior to curing.

21. A method according to claim 19, wherein the polyfunctional amine is an oligomeric aromatic polyfunctional amine selected from the group consisting of:

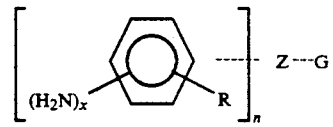

wherein n is an integer ranging from about 2 to about 4; each x is an integer ranging from about 1 to about 2; each phenyl nucleus is para-amino, metaamino, or dimeta-amino substituted; each Z is selected from the group consisting of

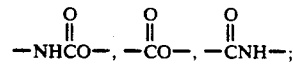

each R is hydrogen or lower alkyl of 4 carbon atoms or less; and G is an n-valent radical which may be obtained by the removal of hydroxyl or amino groups, respectively, from an n-valent polyol or polyamine having an equivalent weight ranging from about 300 to about 3000.

22. A method according to claim 19, wherein the polyfunctional isocyanate is an aromatic polyisocyanate having a functionality ranging from about 2.0 to about 2.5, and wherein said abrasive particles are selected from the group consisting of pumice and alumina, the alumina selected from the group consisting of fused alumina, sintered alumina, calcined alpha alumina, alpha alumina-based ceramic material, and mixtures of these.

23. A method according to claim 19, further comprising the addition of a chain extender to the mixture.

24. A bonded abrasive composition in accordance with claim 19 wherein up to about 80 percent of the polyfunction amine is substituted with a polyfunctional alcohol having active hydrogen functionality of at least 2 and an equivalent weight of at least about 300.

* * * * *

UNITED STATES PATENT AND TRADEMARK OFFICE
CERTIFICATE OF CORRECTION

PATENT NO. : 5,273,559

DATED : December 28, 1993

INVENTOR(S) : Hammar et al.

It is certified that error appears in the above-identified patent and that said Letters Patent is hereby corrected as shown below:

Col. 1, line 10   "07/753,225" should be --07/753,205--

Col. 1, line 28   "idatrices" should be --matrices--

Col. 1, line 29   "4,636,17." should be --4,636,171.--

Col. 1, line 47   "5,011,5121," should be --5,011,512,--

Col. 3, line 9    "Comoositions" should be --Compositions--

Col. 3, Formula

"
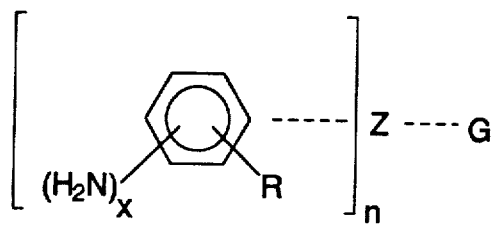
"

should be

--
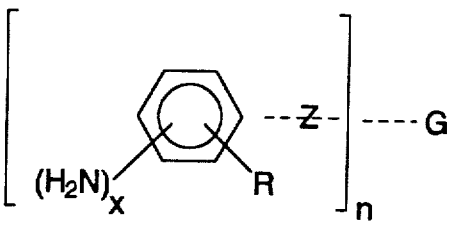
--

UNITED STATES PATENT AND TRADEMARK OFFICE
CERTIFICATE OF CORRECTION

PATENT NO. : 5,273,559
DATED : December 28, 1993
INVENTOR(S) : Hammar et al.

It is certified that error appears in the above-identified patent and that said Letters Patent is hereby corrected as shown below:

| | |
|---|---|
| Col. 8, line 3 | "diluents, fillers, reinforcing fibers" should be --diluents, reinforcing fibers-- |
| Col. 12, line 5 | ">180" should be --<180-- |
| Col. 12, line 7 | "<250" should be -->250-- |
| Col. 14, line 27 | "304" should be --30%-- |
| Col. 16, line 14 | "at least and" should be --at least 2 and-- |
| Col. 16, Formula | |

"
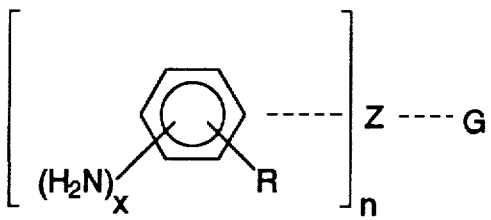
"
should be

--
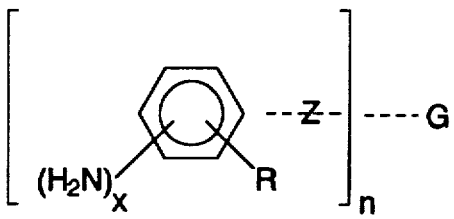
--

UNITED STATES PATENT AND TRADEMARK OFFICE
CERTIFICATE OF CORRECTION

PATENT NO. : 5,273,559

DATED : December 28, 1993

INVENTOR(S) : Hammar et al.

It is certified that error appears in the above-identified patent and that said Letters Patent is hereby corrected as shown below:

Col. 18, Formula

"

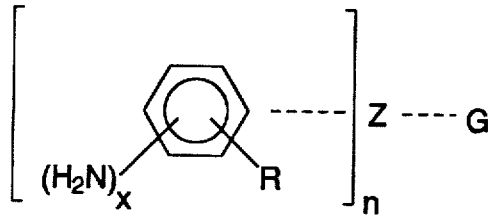

"

should be

UNITED STATES PATENT AND TRADEMARK OFFICE
CERTIFICATE OF CORRECTION

PATENT NO. : 5,273,559
DATED : December 28, 1993
INVENTOR(S) : Hammar et al

It is certified that error appears in the above-indentified patent and that said Letters Patent is hereby corrected as shown below:

--

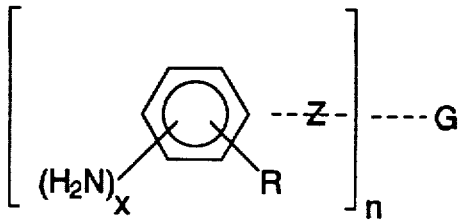

--

Col. 18, line 46    "A bonded abrasive composition" should be --A method--

Col. 18, line 48    "polyfunction" should be --polyfunctional--

Signed and Sealed this

Twelfth Day of July, 1994

Attest:

BRUCE LEHMAN

Attesting Officer    Commissioner of Patents and Trademarks